United States Patent [19]

Otsuki et al.

[11] Patent Number: 4,969,177
[45] Date of Patent: Nov. 6, 1990

[54] X-RAY IRRADIATION APPARATUS PROVIDED WITH IRRADIATION RANGE MONITOR

[75] Inventors: Kunio Otsuki, Uji; Yoshihiko Usui, Osaka, both of Japan

[73] Assignee: Horiba, Ltd., Kyoto, Japan

[21] Appl. No.: 297,759

[22] Filed: Jan. 17, 1989

[30] Foreign Application Priority Data

Jan. 20, 1988 [JP] Japan .................................. 63-11313
Jan. 20, 1988 [JP] Japan .................................. 63-11317

[51] Int. Cl.$^5$ .............................................. A61B 6/08
[52] U.S. Cl. ..................................... 378/206; 378/204
[58] Field of Search .......................................... 378/206

[56] References Cited

U.S. PATENT DOCUMENTS

3,921,001 11/1975 Edholm et al. ...................... 378/206
4,521,905 6/1985 Hosokawa ........................... 378/206

*Primary Examiner*—Craig E. Church
*Attorney, Agent, or Firm*—Price, Gess & Ubell

[57] ABSTRACT

According to the present invention, a laser and X-rays are adapted to be coaxial to each other by the combination of a mirror and a focusing lens, whereby an X-ray irradiation position and a range thereof on an object to be subjected to the application of X-rays can be surely monitored even though the X-ray irradiation range is small.

9 Claims, 5 Drawing Sheets

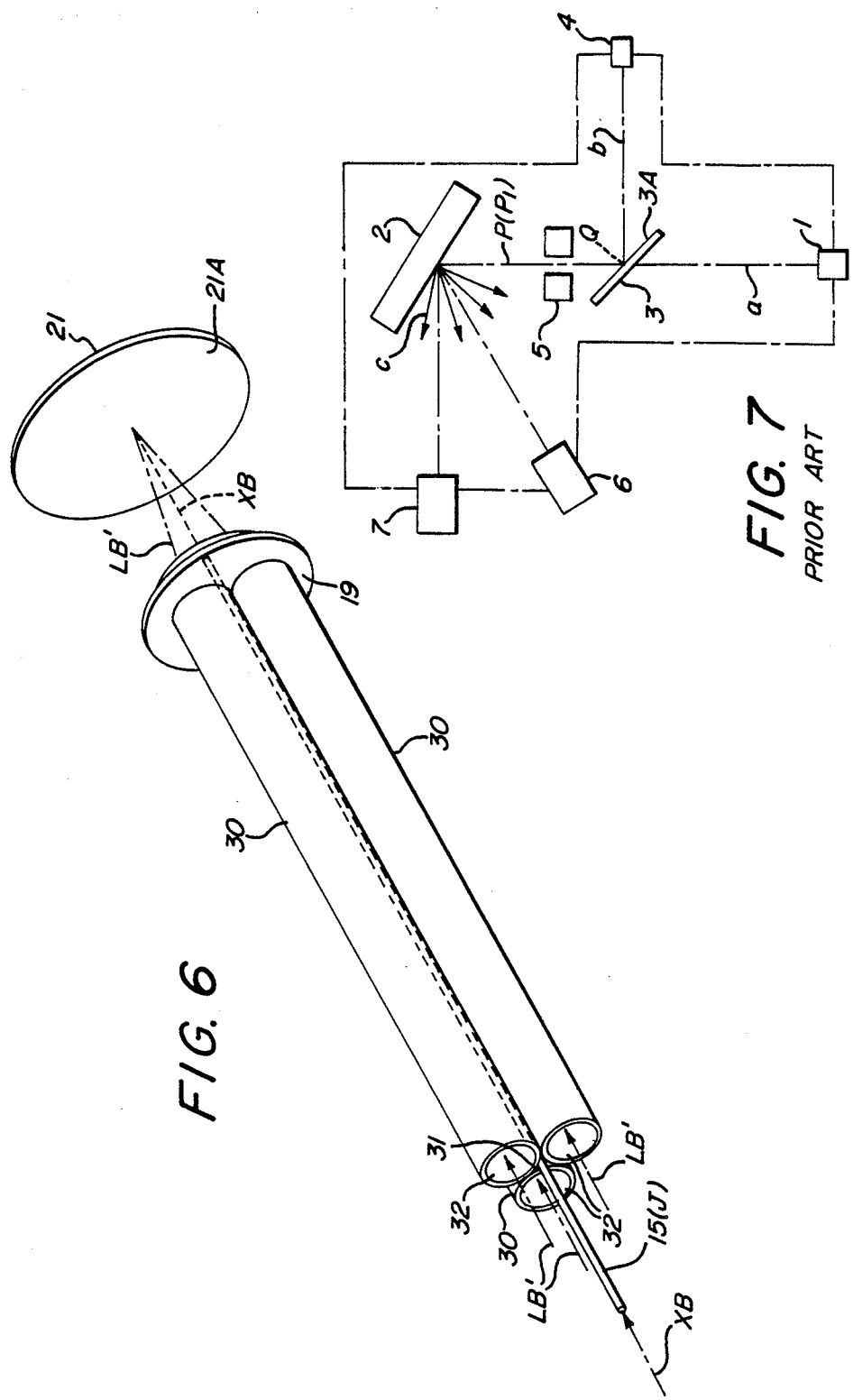

X-RAY IRRADIATION APPARATUS PROVIDED WITH IRRADIATION RANGE MONITOR

BACKGROUND OF THE INVENTION

1. Field of the Invention

The present invention generally relates to an X-ray irradiation apparatus provided with an irradiation range monitor.

2. Description of the Prior Art

A conventional X-ray irradiation apparatus provided with an irradiation range monitor has been disclosed in, for example, Japanese Pat. Laid-Open No. Sho 58-133239. This apparatus, as shown in FIG. 7 herein, comprises an X-ray transmitting mirror 3, which transmits an X-ray a but does not transmit a visible ray b, such as a laser beam. The mirror 3 is provided with a reflecting surface 3A disposed on a downstream side in an X-ray irradiating direction and installed between an X-ray irradiation device 1 and an object 2 to be subjected to the application of X-rays so as to be inclined relative to an axis P of an applied X-ray. A visible light projector 4 is installed so that the visible ray b may be applied to an X-ray transmitting position Q of the reflecting surface 3A, and an axis $P_1$ of a reflected light of the visible ray b may be coaxial or nearly coaxial with the axis P of an applied X-ray. In addition, referring to FIG. 7, reference numeral 5 designates a collimator for converging the X-ray a and the visible ray b so that they may be parallel. Reference numeral 6 designates an X-ray fluorescence analyzer for detecting a fluorescent X-ray c emitted from the object 2 to be subjected to the application of X-rays, and reference numeral 7 designates visible ray projection range-detecting means.

However, with the X-ray irradiation apparatus having the above-described construction, a diameter of the X-ray irradiation range amounts to about 1 mm. In addition, in order to make the diameter of the X-ray irradiation range down to, for example, several ten microns, it is necessary to reduce an inside diameter of the collimator 5 and increase a length of the collimator 5, but it is remarkably difficult to obtain such a construction. Besides, even though such a construction may be achieved, it is difficult to obtain the X-ray irradiation range having the desired diameter, that is, to sufficiently converge the visible ray b which is a guide light. Moreover, it is difficult to monitor a position where the X-ray having a small-sized irradiation range is applied, or a range thereof on the object 2 to be subjected to the application of an X-ray. Accordingly, such monitoring has been hardly conducted with high accuracy when, for example, the object 2 to be subjected to the application of an X-ray is inclined.

SUMMARY OF THE INVENTION

The present invention has been achieved in view of the above-described matters. Thus, it is an object of the present invention to provide an X-ray irradiation apparatus provided with an irradiation range monitor capable of accurately monitoring a position where an X-ray is applied, and a range thereof on an object to be subjected to the application of X-rays even though an irradiation range of X-rays is small-sized.

In order to achieve the above-described objects, an X-ray irradiation apparatus provided with an irradiation range monitor according to the present invention is characterized by a focusing lens disposed apart by a focal distance from an object to be subjected to the application of X-rays, an X-ray guide tube provided with a thin passage for passing X-rays from an X-ray projector therethrough and through a center of an optical axis of the focusing lens for emitting X-rays toward the object to be subjected to the application of X-rays, a mirror inserted into the X-ray guide tube and disposed between the X-ray projector and the focusing lens and inclined so that a reflecting surface thereof may face the focusing lens, and a visible light source for emitting a visible ray to the mirror so that an axis of a reflected light by the reflecting surface of the mirror may be parallel or nearly parallel to the X-ray guide tube.

With the above-described characteristic construction, the visible ray and the X-ray become coaxial by means of the mirror and the focusing lens, whereby the monitoring of the X-ray irradiation range can be accurately achieved regardless of an angle of rotation of the surface of the object to be subjected to the application of X-rays. As a result, the X-rays can be accurately applied to the desired range of the object to be subjected to the application of X-rays.

BRIEF DESCRIPTION OF THE DRAWINGS

One preferred embodiment of the present invention is shown in FIGS. 1 to 3, in which.

In addition.

Figure 5:
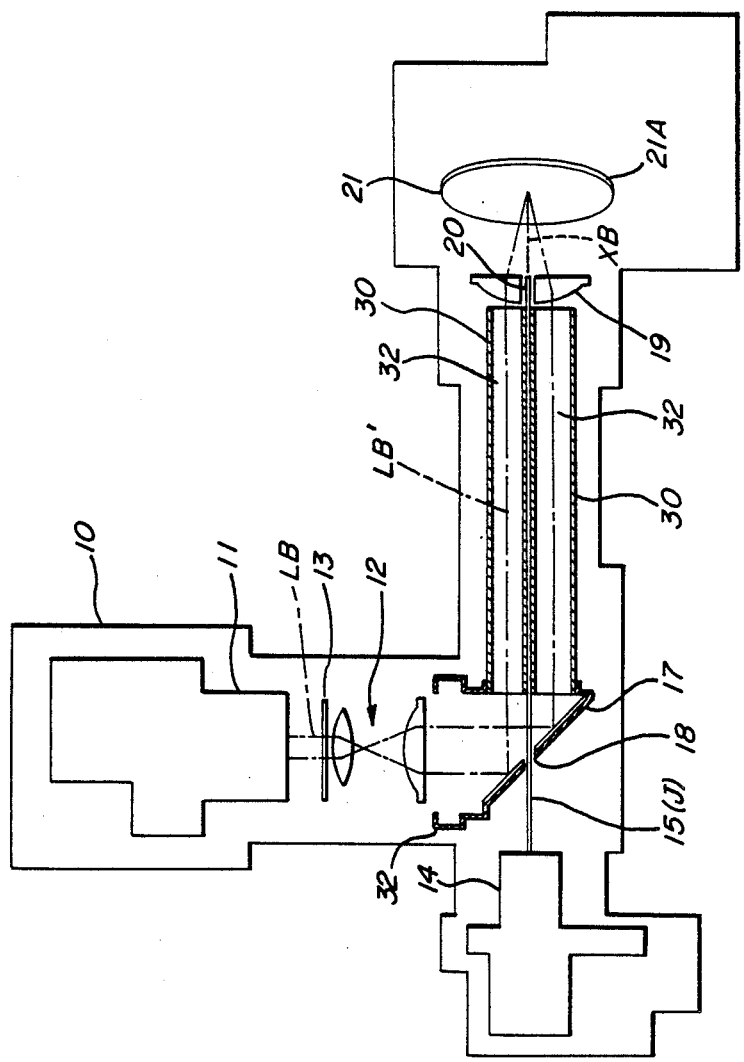

Another preferred embodiment of the present invention is shown in FIGS. 5, 6, in which:

FIG. 5 is a diagram showing one example of an X-ray irradiation apparatus provided with an irradiation range monitor; and FIG. 6 is a perspective view showing principal parts.

FIG. 7 is a diagram showing the prior art.

DETAILED DESCRIPTION OF THE PREFERRED EMBODIMENTS

The preferred embodiments of the present invention will be below-described with reference to the drawings.

Figure 1:
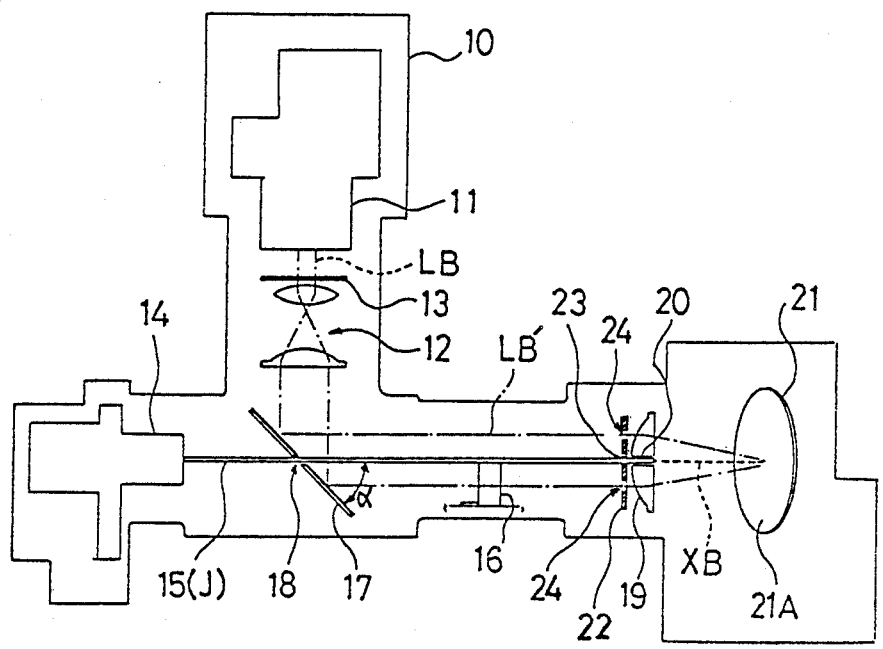
FIG. 1 is a diagram showing one example of an X-ray irradiation apparatus provided with an irradiation range monitor according to the present invention.

Referring now to FIG. 1 showing one example of an X-ray irradiation apparatus provided with an irradiation range monitor according to the present invention, reference numeral 11 designates a laser tube which is a visible light source for emitting a laser beam LB of a visible range. Reference numeral 12 designates a beam expander for regulatedly expanding the laser beam LB to form a parallel beam having an appointed diameter. Reference numeral 13 designates a polarizing plate or a filter for regulating a quantity of laser beam LB. These members 11 to 13 are housed in a housing 10 in a coaxial manner In addition, the housing 10 is formed of, for example, iron or lead so as not to leak X-rays to the outside, and also houses the respective members 14 to 24, which will be mentioned later.

Reference numeral 14 designates an X-ray projector, such as an X-ray tube, disposed at right angles with the laser tube 11 (laser LB). Reference numeral 15 designates an X-ray guide tube disposed so as to meet at almost right angles with the projecting direction of the laser LB and almost horizontally in a line for guiding an X-ray (XB) emitted from the X-ray projector 14. The X-ray guide tube 15 is provided with a thin passage for converging the X-ray XB so that its diameter may amount to about 10 microns, the tube being formed of, for example, glass or metals. In addition, reference numeral 16 designates a holder member suitably disposed for holding the X-ray guide tube 15.

Reference numeral 17 designates a mirror disposed between the X-ray projector 14 and a focusing lens 19, which will be mentioned later, of which reflecting surface 17A is adapted at an appointed angle (for example, an angle α in the drawing is 45 degrees) relative to the installing direction of the X-ray guide tube 15 (hereinafter referred to as X-ray irradiation axis and shown by reference numeral J. The surface 17A reflects the laser LB incident from a direction at about 90 degrees relative to the X-ray irradiation axis J to form a parallel laser LB' along the X-ray irradiation axis J. The mirror 17 is provided with an opening 18 for inserting the X-ray guide tube 15 therethrough, the opening being formed nearly at a center thereof.

The focusing lens 19 is formed of, for example, a convex lens disposed in the vicinity of a pointed end side of the X-ray guide tube 15 such that its optical axis is adapted to be parallel to the X-ray irradiation axis J. The lens 19 is provided with an opening 20 for inserting the X-ray guide tube 15 therein, the opening being formed nearly at a center thereof.

In addition, the above-described mirror 17 and focusing lens 19 are independently provided with an alignment mechanism (not shown).

Reference numeral 21 designates an object to be subjected to the application of X-rays and is disposed at a focal position of the focusing lens 19 and held so as to be movable in all directions, that is, back and forth, up and down, and right and left. It can also be optionally set by a holder (not shown) such that its incident surface 21A is at an angle relative to the X-ray guide tube 15.

Figure 2:
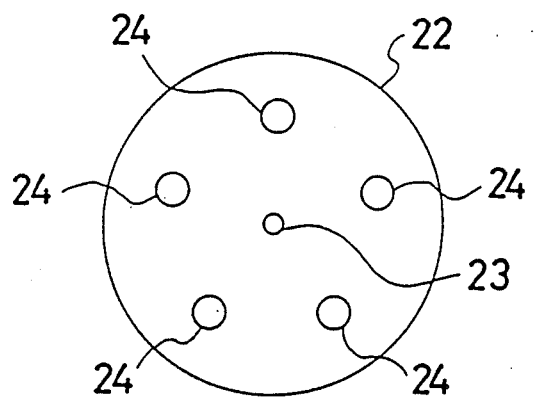
FIG. 2 is a plan view showing one example of a shading member.

Reference numeral 22 designates a shading member of, for example, a disc shape and disposed between the mirror 17 and the focusing lens 19, that is, in the vicinity of the focusing lens 19 in the preferred embodiment shown in the drawing. The shading member 22 is provided with an opening 23 for inserting the X-ray guide tube 15 therein, the opening being formed at a center thereof. It also has five beam-passing through holes 24 formed at positions dividing a concentric circle into five equal parts, with the opening 23 as a center as shown in FIG. 2.

Next, an operation of the X-ray irradiation apparatus provided with an irradiation range monitor having the above-described construction will be below-described with reference to FIG. 3.

At first, the laser tube 11, the beam expander 12, and the polarizing plate 13 are made coincident to each other in an optical axis. The mirror 17 and the focusing lens 19 are regulated by means of their respective alignment mechanisms so that the laser LB' reflected by the mirror 17 may be parallel (coaxial) to the X-ray irradiation axis J.

Under such regulated conditions, [1] when the object 21 exists at a position B in FIG. 3 and a distance between the surface 21A to be subjected to the application of X-rays and the focusing lens 19 (hereinafter referred to as distance L) is equal to a focal distance of the focusing lens 19 (hereinafter referred to as distance F), the laser LB' reflected from the mirror 17 passes through the beam-passing through holes 24 of the shading member 22 and the focusing lens 19 to form an image as one point on the surface 21A, whereby this point of forming an image coincides with the position where the X-ray XB is applied.

Figure 3:
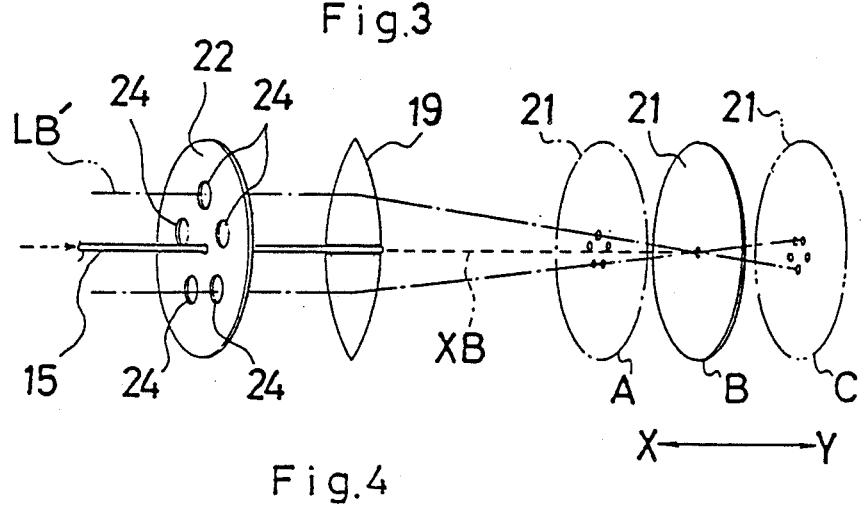
FIG. 3 is an operating diagram.

[2] When the object 21 exists at a position A in FIG. 3 and the distance L is shorter than the distance F, the laser LB' passes through the beam-passing through holes 24 of the shading member 22 and the focusing lens 19 to form an image, which is not reversed in the up and down direction, in short, images (five spots) corresponding to the arrangement condition of the beam-passing through holes 24 on the surface 21A.

In addition, [3] when the object 21 to be subjected to the application of X-rays exists at a position C in FIG. 3 and the distance L is longer than the distance F, the laser LB' passes through the beam-passing through holes 24 and the focusing lens 19 to form an image, which is reversed in the up and down direction, in short, images (five spots) opposite to the arrangement condition of the beam-passing through holes 24 in the up and down direction on the surface 21A.

In the above-described cases [2], [3], it is necessary to only move the focusing lens 19 or the object 21 in the horizontal direction (the direction shown by an arrow XY in FIG. 3) by an appointed distance and make the distance L equal to the distance F.

As shown in the above-described preferred embodiment, the shading member 22 disposed at positions in the upstream side of the focusing lens 19 is provided with the beam-passing through holes 24 so as not to be symmetric in the up and down direction, so that an image formed on the surface 21A by the laser LB', which has passed through the beam-passing through holes 24 and the focusing lens 19 or collection means, is different depending upon the distance L, whereby it can be judged whether the image exists at the focal position of the focusing lens 19 or not.

Under the condition shown in the above-described [1], if the position where the X-ray XB is applied to the surface 21A is quite identical with the position where the laser LB' is focused, both the position where the X-ray XB is applied to the surface 21A and the position where the laser LB is focused coincide with each other regardless of the change of the angle formed between the surface 21A and the X-ray irradiation axis J. Thereby, the irradiation range of the X-rays XB on the surface 21A can be monitored by confirming the position where the laser LB' is incident upon the surface 21A visually or by means of a telescope and the like, whereby the X-rays XB can be accurately incident upon the desired range of the object 21 to be subjected to the application of X-rays.

In addition, according to the above-described EXAMPLE, unless the laser LB' incident upon the focusing lens 19 is parallel to an optical axis of the focusing lens 19 (or vertical to the surface of the lens), the number of the spots formed on the surface 21A is reduced or the brilliancy is not uniform even though all spots are formed, so that the condition of the laser LB' incident upon the focusing lens 19 also can be confirmed.

Figure 4:
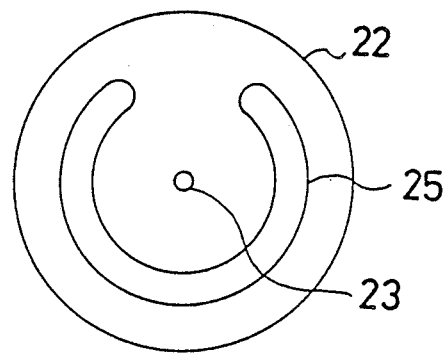
FIG. 4 is a plan view showing another example of a shading member.

The present invention is not limited by the above-described EXAMPLE. For example, the beam-passing through holes formed in the shading member 22 may be formed as one opening 25, which is not symmetrical in the up and down direction (symmetrical in the right and left direction), as shown in FIG. 4.

In addition, the above-described beam-passing through holes 24 and opening 25 may not be symmetrical in the right and left direction or may not be symmetrical in both the up and down direction and the right and left direction.

Referring to FIGS. 5, 6 showing different EXAMPLES of the present invention, a member for holding the X-ray guide tube 15 is also used as the shading member. Referring to both drawings, reference numerals 30 designate ray guide pipes formed of metals, such as stainless steel or aluminum, or other materials, the X-ray guide tube 15 being inserted into a space 31 having a reverse triangular shape as seen in the section formed by piling up these beam guide pipes 30 in parallel to each other and in a triangular shape as seen in the section to be horizontally held. Internal spaces 32 of the respective beam guide pipes 30 are formed as beam-passing through holes through which the laser LB' reflected by the mirror 17 passes.

The X-ray irradiation apparatus provided with an irradiation range monitor having the above-described construction operates in the same manner as in the above-described EXAMPLE, so that the description of the operation is omitted. This EXAMPLE shows an advantage in that the X-ray guide tube 15 can be still more surely horizontal and linear.

In addition, in the above-described respective EXAMPLES, for example, the laser tube 11, the beam expander 12 and the polarizing plate 13 may be housed in a housing pipe so that their optical axes may coincide with each other and house this housing pipe in the housing 10.

In addition, it is not always required to set the angle α formed between the mirror 17 and the X-ray irradiation axis J at 45 degrees, but it may be set at an optional angle. Also, every arrangement in which the laser LB' reflected by the mirror 17 becomes coaxial with the X-ray irradiation axis J can be used.

In addition, a visible light source emitting visible rays may be used in place of the laser tube 11 emitting the laser LB of visible range.

As described above, the X-ray irradiation apparatus provided with an irradiation range monitor according to the present invention is adapted to make the laser and the X-rays coaxial to each other by means of the mirror and the focusing lens, so that the X-ray irradiation range can be accurately monitored and the X-rays can be accurately applied to the desired range of the object to be subjected to the application of X-rays, regardless of the rotating angle of the surface to be subjected to the application of X-rays.

When the shading member with the beam-passing through holes, which are not symmetrical in the up and down direction or the right and left direction, is provided in the upper reaches of the focusing lens in addition to the above-described construction, the X-ray irradiation range can be accurately monitored regardless of the rotating angle of the surface to be subjected to the application of X-rays and the position of the surface to be subjected to the application of X-rays can be found by observing the condition of the formation of the image on the surface to be subjected to the application of X-rays, whereby the X-rays can be accurately applied to the desired area of the object to be subjected to the application of X-rays by suitably moving the focusing lens or the object on the basis of the observed condition.

In particular, the present invention is effective in the case where the X-ray irradiation range or area on the surface to be subjected to the application of X-rays is minute (for example, about 10 microns in diameter).

What is claimed is:

1. An X-ray irradiation apparatus provided with an irradiation position monitor, comprising:
    an X-ray source;
    a focusing lens disposed apart by a focal distance from an object to be subjected to the application of X-rays;
    an X-ray guide tube provided with a thin passage for passing X-rays from the X-ray source therethrough from an X-ray projector through a center of an optical axis of said focusing lens and for emitting said X-ray toward said object;
    a mirror inserted about said X-ray guide tube and disposed between said X-ray projector and said focusing lens while being inclined so that a reflecting surface thereof may face said focusing lens;
    a visible light source for emitting visible rays to said mirror so that an axis of a reflected light by said reflecting surface of said mirror may be parallel or nearly parallel to said X-ray guide tube, and
    means for creating a visible target image with the light source rays whereby the focusing lens can form the target image to define the position of the X-rays.

2. An X-ray irradiation apparatus provided with an irradiation position monitor as set forth in claim 1, wherein the image-creating means further includes a shading member provided with beam-passing through holes, which are not symmetrical in the up and down direction or the right and left direction, said shading member disposed between said mirror and said focusing lens.

3. An X-ray irradiation apparatus provided with an irradiation position monitor as set forth in claim 2, wherein said shading member is disc-like in shape.

4. An X-ray irradiation apparatus provided with an irradiation position monitor as set forth in claim 2, wherein said shading member can be used also as a holding member of said X-ray guide tube.

5. An X-ray irradiation apparatus as set forth in claim 1 wherein the image creating means further includes a plurality of elongated tubes positioned about the X-ray guide tube and dividing the visible light rays.

6. An X-ray irradiation and irradiation position monitoring apparatus, comprising:
    X-ray source means for emitting X-rays along an irradiation axis including an X-ray guide tube;
    visible light source means for emitting visible light rays in a direction generally perpendicular to said irradiation axis;
    reflection means for reflecting said visible light rays to thereby produce reflected rays;
    a shading member to create a target image in the visible light rays, and
    focusing means for collecting said visible reflected rays and directing them towards an object to be irradiated, whereby the target image can define the position of the X-rays.

7. The apparatus according to claim 5 wherein said reflection means comprises a mirror having a reflecting surface angularly disposed to said irradiation axis.

8. The apparatus according to claim 5 wherein said focusing means comprises a focusing lens having an optical axis generally coaxial to said irradiation axis.

9. The apparatus according to claim 6 wherein said visible light source means comprises a laser tube and a polarizing plate coaxially aligned with a beam expander.

* * * * *